United States Patent [19]
Chao

[11] Patent Number: 5,928,858
[45] Date of Patent: Jul. 27, 1999

[54] PETRI DISH WITH REMOVABLE LOCATION MARKINGS AND METHOD OF MAKING THE SAME

[76] Inventor: David M. Chao, 6 Garden Ct., Apt. 2, Cambridge, Mass. 02138

[21] Appl. No.: 08/897,156

[22] Filed: Jul. 18, 1997

[51] Int. Cl.[6] .............................. C12Q 1/00; C12M 3/00
[52] U.S. Cl. ............................ 435/4; 435/30; 435/288.3; 435/305.1; 435/307.1
[58] Field of Search .............................. 435/4, 30, 288.3, 435/288.4, 305.1, 305.2, 305.4, 307.1; 422/102

[56] References Cited

U.S. PATENT DOCUMENTS

| | | |
|---|---|---|
| 2,772,650 | 12/1956 | Cook . |
| 3,010,880 | 11/1961 | Littman et al. . |
| 3,065,150 | 11/1962 | Kravitz . |
| 3,197,384 | 7/1965 | Goldman . |
| 3,227,522 | 1/1966 | Salisbury, Jr. et al. . |
| 3,347,179 | 10/1967 | Haidinyak . |
| 3,684,660 | 8/1972 | Kereluk et al. . |
| 4,100,676 | 7/1978 | Ferguson ................................... 30/292 |
| 4,598,050 | 7/1986 | Brown ...................................... 435/298 |
| 4,945,061 | 7/1990 | Iskander ................................... 435/298 |
| 5,061,621 | 10/1991 | Perlman ..................................... 435/30 |
| 5,232,838 | 8/1993 | Nelson et al. ............................. 435/30 |
| 5,476,016 | 12/1995 | Fedorka-Cray et al. .................. 73/863 |
| 5,571,721 | 11/1996 | Turner .................................. 435/305.1 |

OTHER PUBLICATIONS

"Innovative Technology for Life Science Advancement", Stratagene Cloning Systems, 1997.
Replica Plating Grid, SCIENCEWARE, VWR Scientific Products Corporation, 1997/1998 Catalog.

*Primary Examiner*—David A. Redding
*Attorney, Agent, or Firm*—Burns Doane Swecker & Mathis, L.L.P.

[57] ABSTRACT

A removable marking sticker is provided for a Petri dish for correlating a cell on a Petri dish with a specific location. The sticker includes a backing substrate and a removable sticker element having an adhesive surface immediately adjacent to the backing substrate. The sticker has a plurality of dividing lines designated thereon in a predetermined configuration so as to define a plurality of locations.

9 Claims, 5 Drawing Sheets

PETRI DISH WITH REMOVABLE LOCATION MARKINGS AND METHOD OF MAKING THE SAME

BACKGROUND OF THE INVENTION

1. Field of the Invention

The present invention relates generally to a Petri dish, and more particularly, to a Petri dish with predetermined sectors or grid pattern removably marked thereon, a marking sticker and a method of marking for obtaining the same.

2. Description of the Related Art

The study of microorganisms, such as yeast, bacteria, fungi, viruses, and the like, often require the growth of the same on a solid medium. One method for growing microorganisms on solid media is to use a Petri dish filled with a solidified agar. This is collectively referred to as a plate. Depending upon the experimental situation, the type of medium used in the agar plate may be considered rich, minimal, or an indicator.

The study of microorganisms also often require that cells placed on a plate be marked or labelled in some fashion in order to later distinguish one cell from an adjacent cell. This is particularly true when isolating single colonies of bacterial strains and when storing the same. Heretofore, the most cost efficient and simplest manner to accomplish this task was to draw the desired grids or sectors on the bottom of the Petri dish using a pen or permanent marker and ruler. This process, however, was quite time consuming for the scientist and often led to significant variation from one plate to another.

Another alternative, that was specifically designed to assist the scientist in replica plating, was a large opaque plate or holder having five wells that each hold one Petri dish. Typically, two wells were preprinted with a twenty-four square numbered grid and two wells were preprinted with a fifty square numbered grid. The center well was generally unnumbered and holds the main Petri dish containing the discrete colonies to be transferred. Thus, an unused Petri dish was placed in each well overtop of the preprinted grid and cells or microorganisms from the main dish were transferred to a prenumbered location within the Petri dish of each well.

Unfortunately, the Petri dishes within the wells had a tendency to shift during use, thereby causing misalignment with the preprinted wells therebelow and potential errors in the transfer procedure. Further, since the behavior of the microorganisms on the plate must be correlated with their particular sample location and number, the Petri dishes must be examined while they are positioned overtop of the preprinted wells. Not only was this inconvenient to the scientist, but misalignment of the Petri dish and the well may lead to inaccurate experiment results.

The use of the preprinted holder also required the individual Petri dishes as well as the holder to remain horizontal during the process. That is, the Petri dishes must be horizontal within the wells of the holder in order for the preprinted information to be visible to the user. This position, however, may become uncomfortable to the scientist during the transfer process. In addition, it is sometimes advantageous, particularly when relatively opaque growth media is used, to shine light through the Petri dish in order to better visualize the markings thereon as well as the microorganisms growing on the surface of the agar. Such preprinted holders of the prior art, however, were generally opaque, thereby preventing illumination of the markings and the growing microorganisms.

A further Petri dish available in the prior art to assist the scientist in identifying specific microorganisms was one having a grid or sector configuration molded into the bottom surface thereof. The molded dividing lines were generally difficult to see during the transfer process and while recording experiment results, however, and the scientist was still required to perform the time consuming chore of hand numbering or otherwise labelling each of the individual grid squares or sectors. The molded dishes also prevented the removal of the grid pattern when desired, such as, for instance to photographically record the results of an experiment. Most significantly though, since each configuration of grids or sectors required a different set of Petri dishes to be kept in inventory, the purchase and stocking costs associated with the molded Petri dishes was quite prohibitive.

Accordingly, there is a need for a simple and cost-efficient mechanism for marking Petri dishes in order to thereby obtain correlation of particular microorganisms on a plate with a predetermined sample location number or other label.

SUMMARY OF THE INVENTION

Accordingly, it is an object of the present invention to provide a Petri dish with location markings that overcomes the disadvantages of the prior art.

The present invention achieves this and other objects through the provision of a removable marking sticker for a Petri dish for correlating a cell on a Petri dish with a specific location. The sticker includes a backing substrate and a removable sticker element having an adhesive surface immediately adjacent to the backing substrate. The sticker has a plurality of dividing lines designated thereon in a predetermined configuration so as to define a plurality of locations. The plurality of dividing lines preferably form a plurality of squares in a grid configuration or, alternatively, a plurality of pie-shaped sectors.

The present invention further provides a Petri dish including a base unit having a bottom portion and a wall portion extending upward therefrom, with the bottom portion having an upper surface and a lower surface. A removable marking element defining a plurality of predetermined locations is applied to the lower surface of the bottom portion, with the marking element being visible through the upper surface of the base unit. The removable marking element enables correlation between microorganisms within the base unit and one of the plurality of predetermined locations. The removable marking element preferably includes a plurality of dividing lines defining the plurality of predetermined locations, which may be a plurality of squares in a grid configuration or a plurality of pie-shaped sectors, for example.

BRIEF DESCRIPTION OF THE DRAWINGS

These, and other, objects, features and advantages of the present invention will become more readily apparent to those skilled in the art upon reading the following detailed description, in conjunction with the appended drawings, in which.

DETAILED DESCRIPTION OF THE PREFERRED EMBODIMENTS

Figure 1:
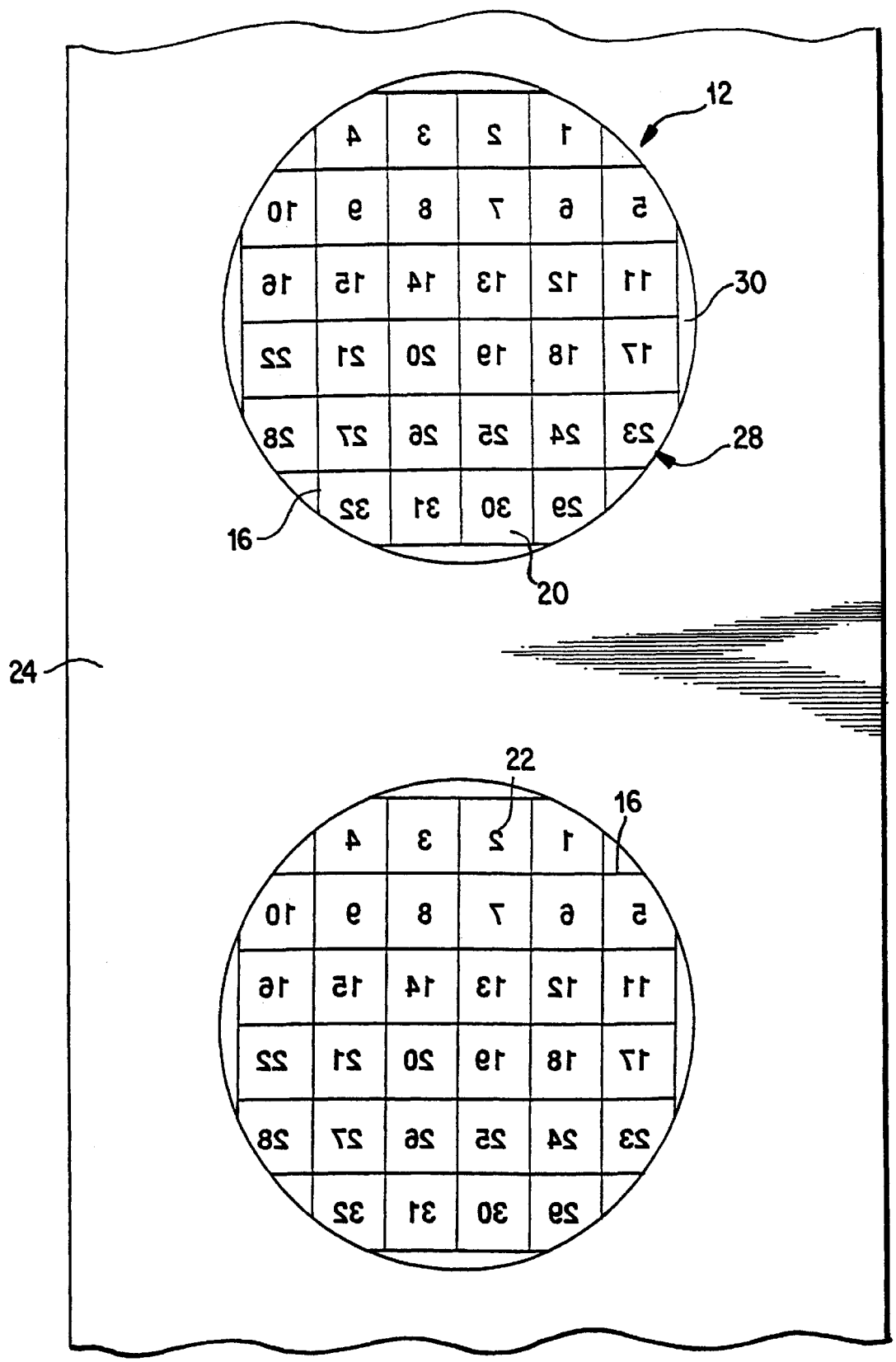
FIG. 1 is a top plan view of a sheet of marking stickers in accordance with the present invention.
Figure 2:
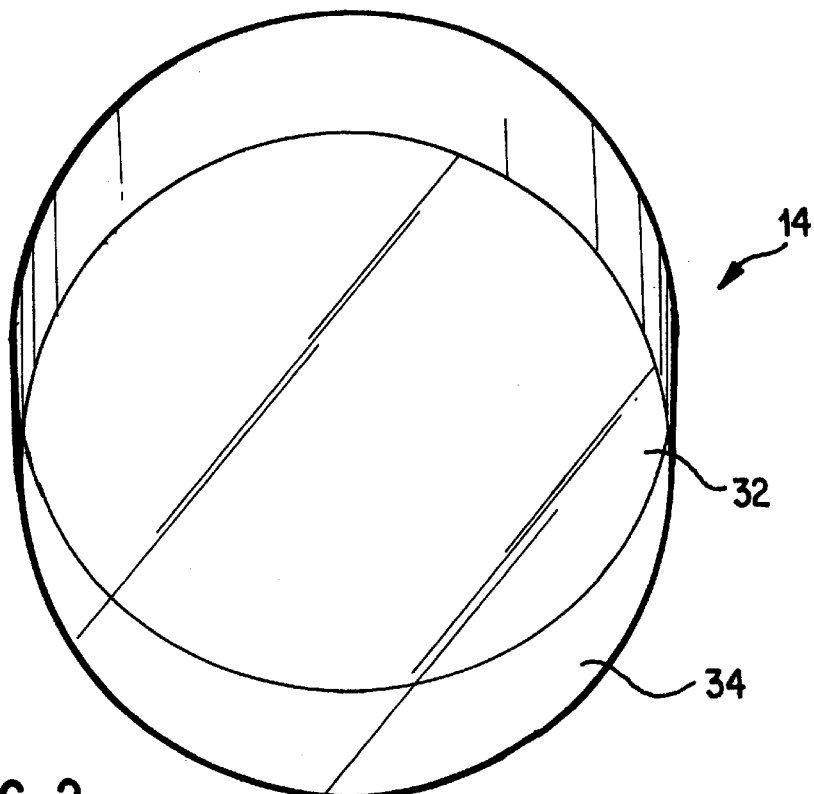
FIG. 2 is a top perspective view of a conventional Petri dish.
Figure 3:
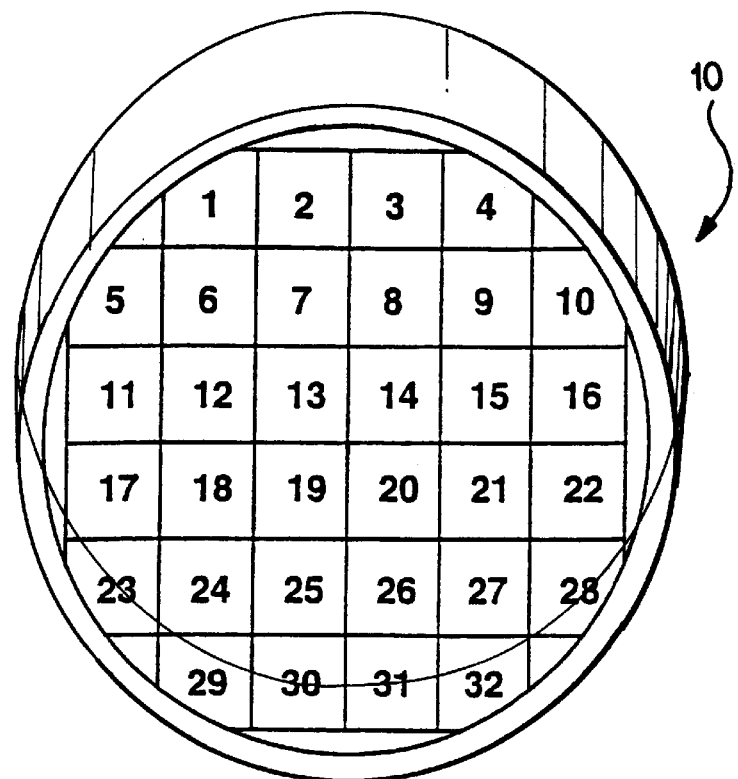
FIG. 3 is a top perspective view of a Petri dish in accordance with the present invention.
Figure 4:
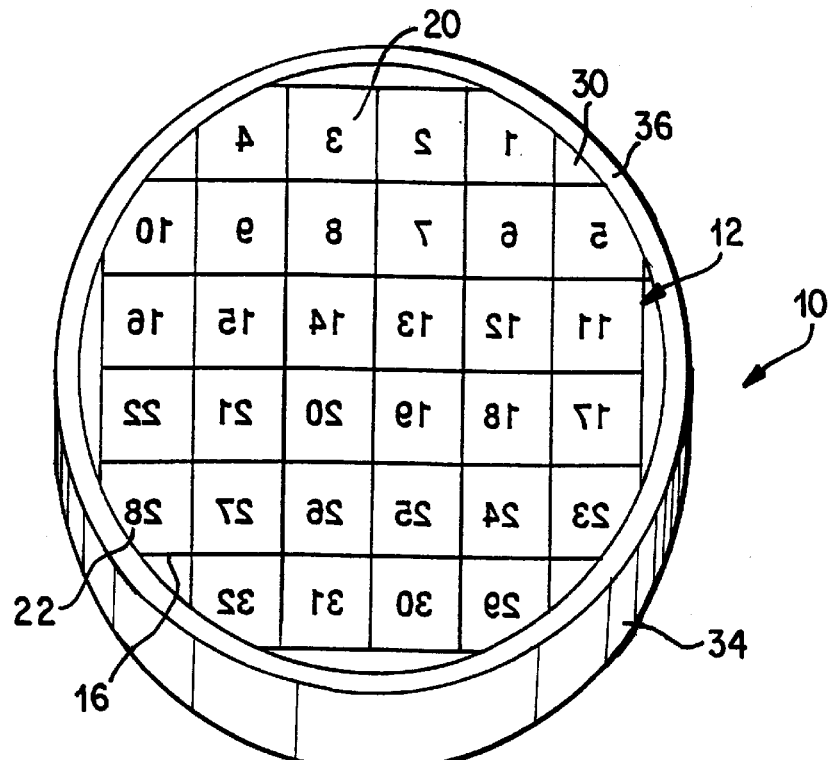
FIG. 4 is a bottom perspective view of the Petri dish shown in FIG. 3.
Figure 6:
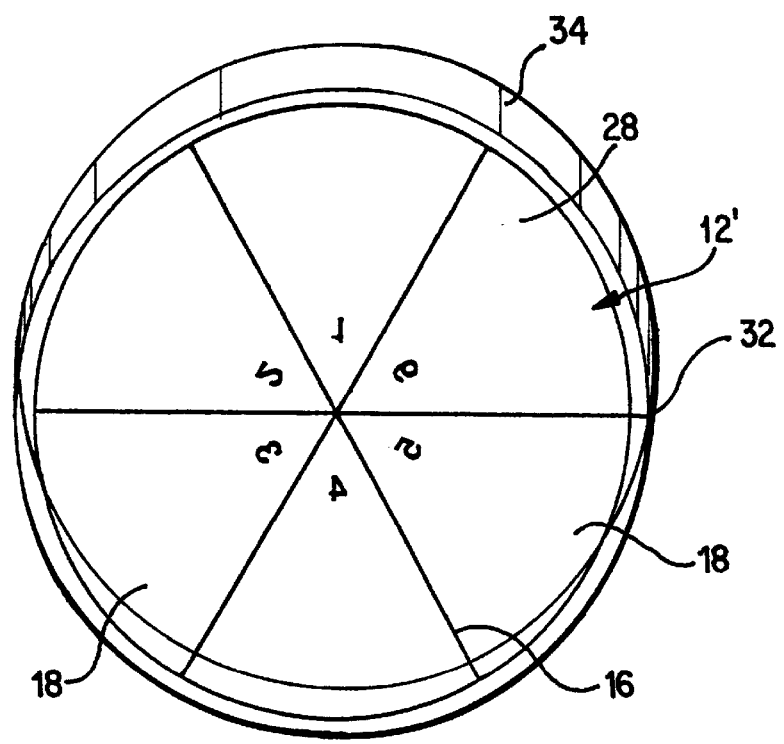
FIG. 6 is a further embodiment of a Petri dish in accordance with the present invention.
Figure 5:
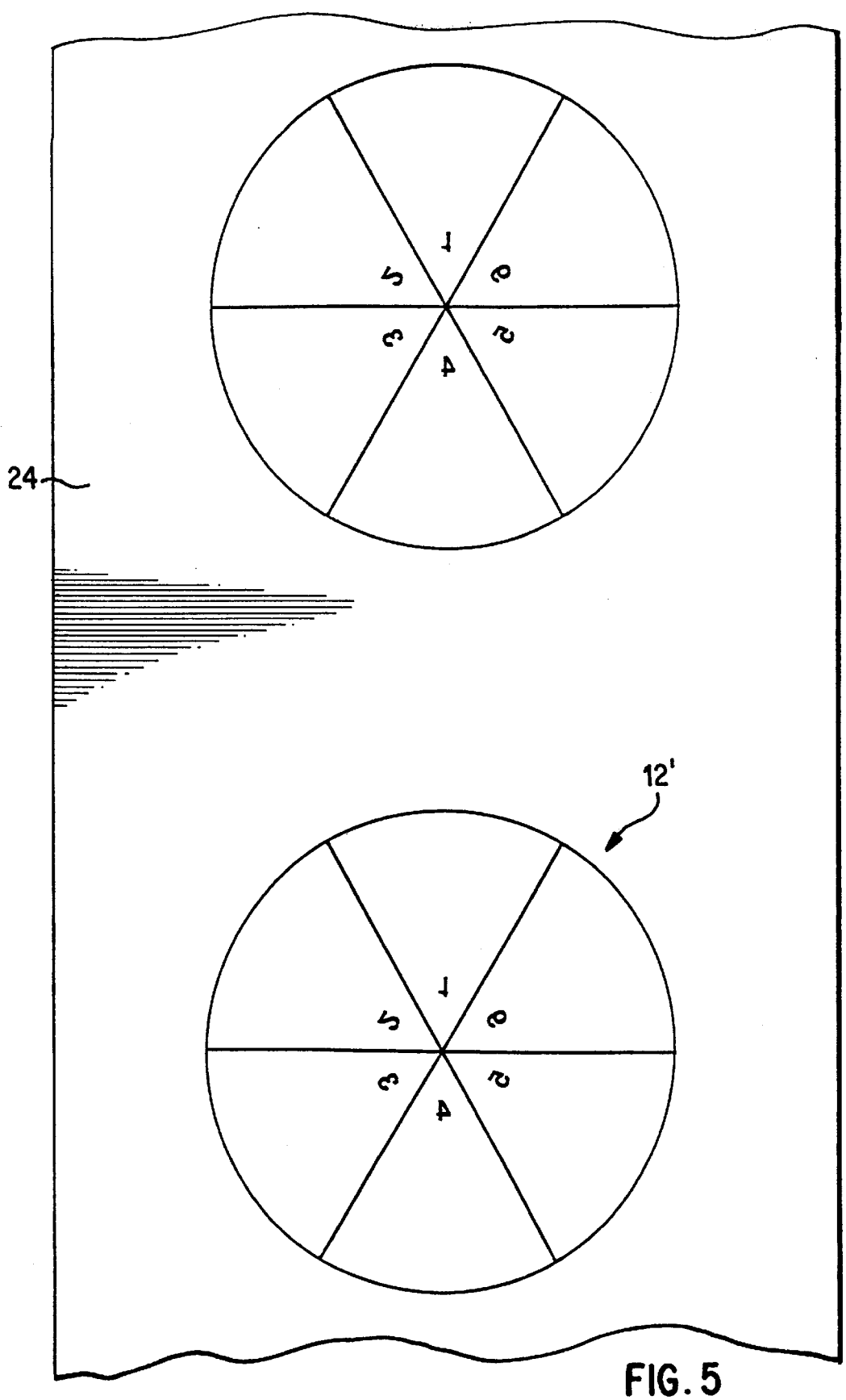
FIG. 5 is a further embodiment of a sheet of marking stickers in accordance with the present invention.

Referring to FIGS. 1–3, a Petri dish with removable location markings according to the present invention is shown generally by reference numeral 10. Petri dish 10 is produced in accordance with the present application by applying a pre-printed, self-adhesive marking sticker 12 to a conventional Petri dish 14, as shown in FIG. 2. The marking sticker may include location markings in the form of sectors, as shown in FIG. 5 for sticker 12', a grid, as shown in FIG. 1 for sticker 12, or any other pattern or configuration that may be desired.

The Petri dish 14 is typically a transparent plastic dish having a cooperating cover (not shown). The Petri dish 14 includes a bottom portion 32 and an upstanding wall portion 34 extending therearound. Petri dishes come in many different shapes and sizes, such as a one hundred millimeter square, a sixty millimeter circle, a one hundred millimeter circle, or a two-by-six array of ten millimeter circles, for example.

The marking sticker 12 is preferably die-cut in a conventional manner from a plastic material, such as a laser imprintable, adhesive-backed polyester sheet. The sticker may be clear and transparent, colored and transparent, opaque and colored, reflective, or any combination thereof depending upon the specific lighting conditions required to improve visualization of the microorganisms and the desired marking. Although the marking stickers 12, 12' may be supplied individually, a plurality of marking stickers 12, 12' will generally be provided on a common sheet or roll of a backing substrate 24. The marking sticker 12, 12' preferably includes a adhesive surface 28 adjacent to the backing substrate 24 and a non-adhesive surface 30 on the opposite side thereof. Each marking sticker 12, 12' includes a plurality of dividing lines 16 printed thereon to thereby define the various rectangular grid or sector markings. The dividing lines 16, in the illustrated examples, form the six pie-shaped sectors 18 shown in FIG. 5 and the thirty-two squares 20 of the grid shown in FIG. 1. Each of the sectors 18 and squares 20 may further include an indicator 22 such as a numeral or any other type of label or alpha-numeric indicator that may be used to define a location within the grid. The size of the marking sticker 12, 12' generally corresponds to the size of the Petri dish to be used. That is, for a sixty millimeter circular Petri dish, a sixty millimeter circular sticker would preferably be utilized. It should be apparent to one skilled in the art that the size of the marking sticker 12, 12' as well as the number and size of the defined grid or sector and the indicator or label to be used may vary depending upon the Petri dish to which it is applied and the needs of the user.

In order to form Petri dish 14, a marking sticker 12, 12' is first removed from the backing substrate sheet 24. The sticker 12, 12' should correspond in size to the Petri dish 14 to be used and have the desired location marking and illumination characteristics required for the selected experiment. After removal from the backing substrate 24, the adhesive surface 28 of the sticker 12, 12' is applied to a bottom surface 36 of the Petri dish 14. The numeric indicators 22 may be printed on the self-adhesive surface 28 of the sticker 12, 12'. Alternatively, when the marking sticker is generally clear, the numeric indicators may be printed on the non-adhesive surface 30 if it so desired, with the alpha-numeric indicators 22 being a mirror image when necessary in order to obtain proper orientation of the indicators 22 for viewing from a position above the top surface of the Petri dish, such as shown in FIG. 3. The sticker 12, 12' is preferably evenly applied to the bottom surface of the Petri dish without wrinkles or bubbles in order to provide a clear viewing thereof during use.

The stickers 12 of the present invention, in addition to being preprinted and supplied to the end user, may also be customized by the end user. The stickers 12 are die-cut on the adhesive-backed polyester sheets, as described above, but in this instance the stickers 12 have no markings or alternatively, they have sectors or a grid marked thereon but no numeric indicators. The sheets on which the stickers are provided are laser imprintable, however, such that the end user may customize the markings and/or the numeric indicators to be used with a conventional laser printer. Thus, any configuration of grid or sector markings and/or any type of alpha-numeric indicator may be placed on the stickers by the end user merely be printing the same on a printer.

Figure 7:
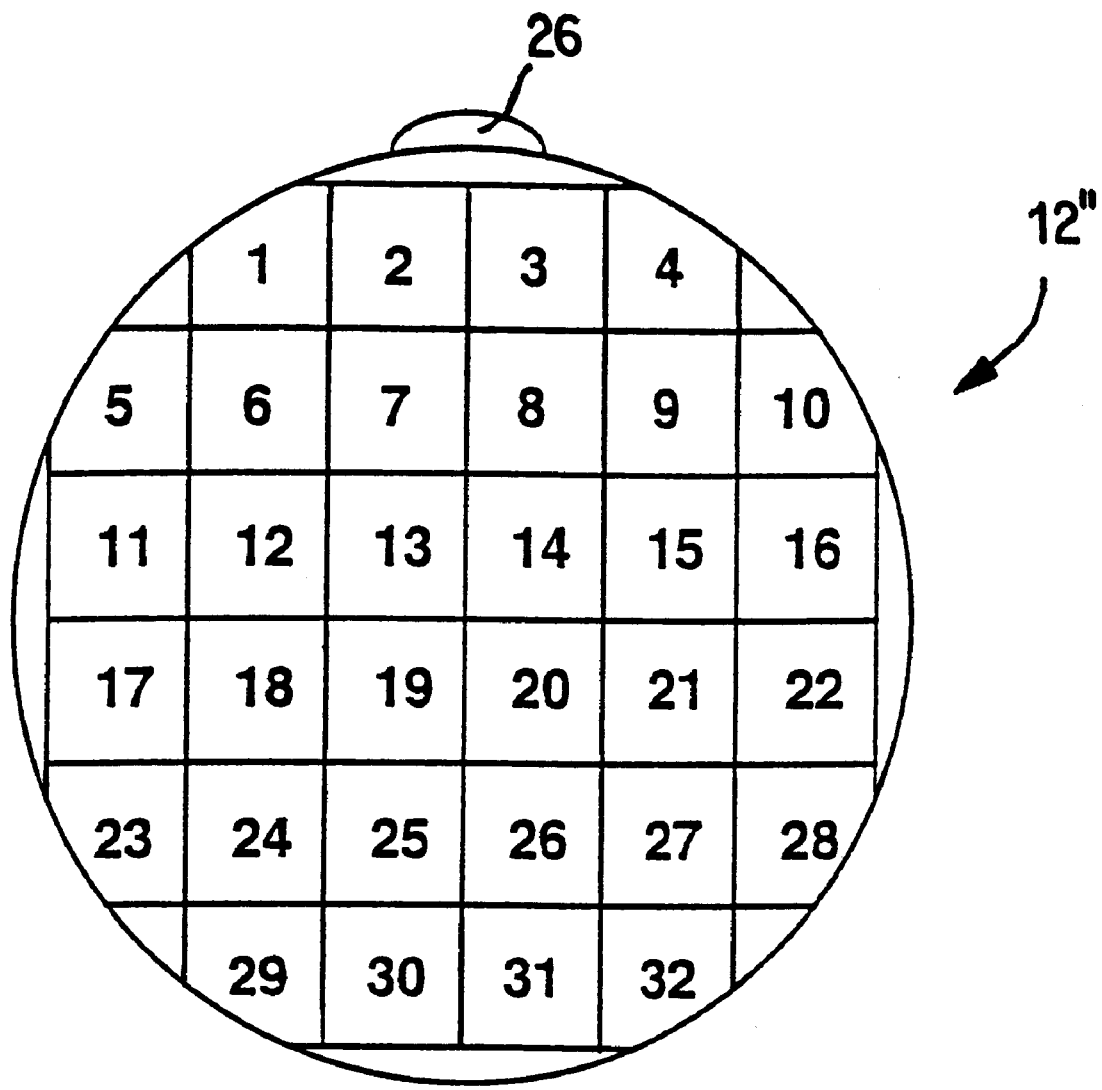
FIG. 7 is a further embodiment of a marking sticker in accordance with the present invention.

Referring to FIG. 7, a further variation of the present invention includes a marking sticker 12" having a projecting tab 26 to assist in applying and removing the sticker from the bottom surface of the Petri dish. Preferably, the tab 26 is non-adhesive. The sticker 12" may be supplied individually or with a plurality of stickers 12" on common backing sheet 24, as described above with respect to the earlier embodiments.

While the present invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A Petri dish comprising:

a base unit having a bottom portion and a wall portion extending upward therefrom, said bottom portion having an upper surface and a lower surface;

a removable marking means defining a plurality of predetermined locations applied to the lower surface of said bottom portion, said marking means being visible through said upper surface of said base unit, and said removable marking means enabling correlation between microorganisms within said base unit and one of said plurality of predetermined locations.

2. The Petri dish of claim 1, wherein said removable marking means comprises a marking sticker including a removable sticker element.

3. The Petri dish of claim 2, wherein said sticker includes an adhesive surface and a non-adhesive surface.

4. The Petri dish of claim 2, wherein said sticker includes a plurality of dividing lines defining said plurality of predetermined locations.

5. The Petri dish of claim 4, wherein said plurality of dividing lines define a plurality of squares in a grid configuration.

6. The Petri dish of claim 4, wherein said plurality of dividing lines form a plurality of pie-shaped sectors.

7. The Petri dish of claim 1, wherein said plurality of predetermined locations are identified with an indicator.

8. The Petri dish of claim 7, wherein said indicator includes an alpha-numeric indicator.

9. A method of forming a Petri dish with predetermined location markings, said method comprising the steps of:

provilding a Petri dish having a base unit with a bottom portion and a wall portion extending upwards therefrom, the bottom portion including an upper surface and a lower surface;

providing a self-adhesive marking sticker removably disposed on a backing substrate, the sticker having an adhesive surface adjacent to the backing substrate and a non-adhesive surface opposite thereto;

removing the sticker from the backing substrate; and applying the adhesive surface of the sticker to the bottom surface of the Petri dish. an alpha-numeric indicator.

* * * * *